(12) United States Patent
Kesten et al.

(10) Patent No.: US 7,923,455 B2
(45) Date of Patent: Apr. 12, 2011

(54) MEDICAMENTS FOR THE PREVENTION OR TREATMENT OF HEART FAILURE COMPRISING ADMINISTRATION OF AN ANTICHOLINERGIC

(75) Inventors: Steven Kesten, Southbury, CT (US); Klaus Viel, Mainz (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 609 days.

(21) Appl. No.: 11/332,646

(22) Filed: Jan. 13, 2006

(65) Prior Publication Data
US 2006/0173038 A1 Aug. 3, 2006

Related U.S. Application Data

(60) Provisional application No. 60/648,012, filed on Jan. 28, 2005.

(51) Int. Cl.
*A61K 31/44* (2006.01)
(52) U.S. Cl. .......... 514/291; 514/929; 514/930
(58) Field of Classification Search .......... 514/291
See application file for complete search history.

(56) References Cited

FOREIGN PATENT DOCUMENTS
WO WO 2005/007142 A2 1/2005

OTHER PUBLICATIONS

Uren et al. (Eur Heart J. (Jun. 1993); 14(6):744-50).*
Gross et al. (Chest. (Dec. 2004); 126(6):1946-53).*
Cedars-Sinai ("Health Conditions: Congestive Heart Failure"; http://www.csmc.edu/5655.html (2007)).*
Fiutowski et al. (Kardiol Pol. Dec. 2004;61(12):561-9; discussion 570).*
Rasche, K. et al., "Pulmo Cardials: Effect inhalativer Bronchodilatatoren auf den Atemwegswiderstand bei acuter inksventrikluaerer Funktionsstoerung," Pneumologie, Berlin, Germany, vol. 44 No. Suppl. 1, Feb. 1990, pp. 533-535, XP000924970.
Kindman, L. Allen et al., "Abnormalities of pulmonary function in patients with congestive heart failure, and reversal with ipratropium bromide," American Journal of Cardiology, vol. 73 No. 4, 1994, pp. 258-262, XP008073517.
Rolla, G. et al., "Bronchodilating effect of ipratropium bromide in heart failure," European Respiratory Journal, vol. 6 No. 10, 1993, pp. 1492-1495, XP008073532.
Kindman, L.A. et al., "Pulmonary abnormalities in congestive heart failure reversal by the inhaled anticholinergic agent ipratropium bromide," Journal of the American College of Cardiology, vol. 19 No. 3 Suppl. A, 1992, p. 161A, XP008073531.
Yesildag, O. et al., "Pulmonary abnormalities in congestive heart failure: reversal by the inhaled anticholinergic agent ipratropium bromide," European Heart Journal, vol. 21 No. Abstract Suppl., Aug. 2000, ph. 660, XP008073533.
Khan, K.A. et al., "Pulmonary function profle in chronic congestive heart failure and the effect of heart ipratropium bromide," Indian Heart Journal, 2000, India, vol. 52 No. 3, pp. 297-300, XP008073530.

* cited by examiner

*Primary Examiner* — Frederick Krass
*Assistant Examiner* — Chris E Simmons
(74) *Attorney, Agent, or Firm* — Michael P. Morris; Wendy A. Petka

(57) ABSTRACT

The present invention relates to a method for the prevention or the treatment of heart failure comprising administration of a therapeutically effective amount of an anticholinergic 1, medicaments for the prevention or treatment of heart failure comprising one or more, preferably one anticholinergic 1, and methods for the preparation of these medicaments.

2 Claims, 1 Drawing Sheet

Figure 1:
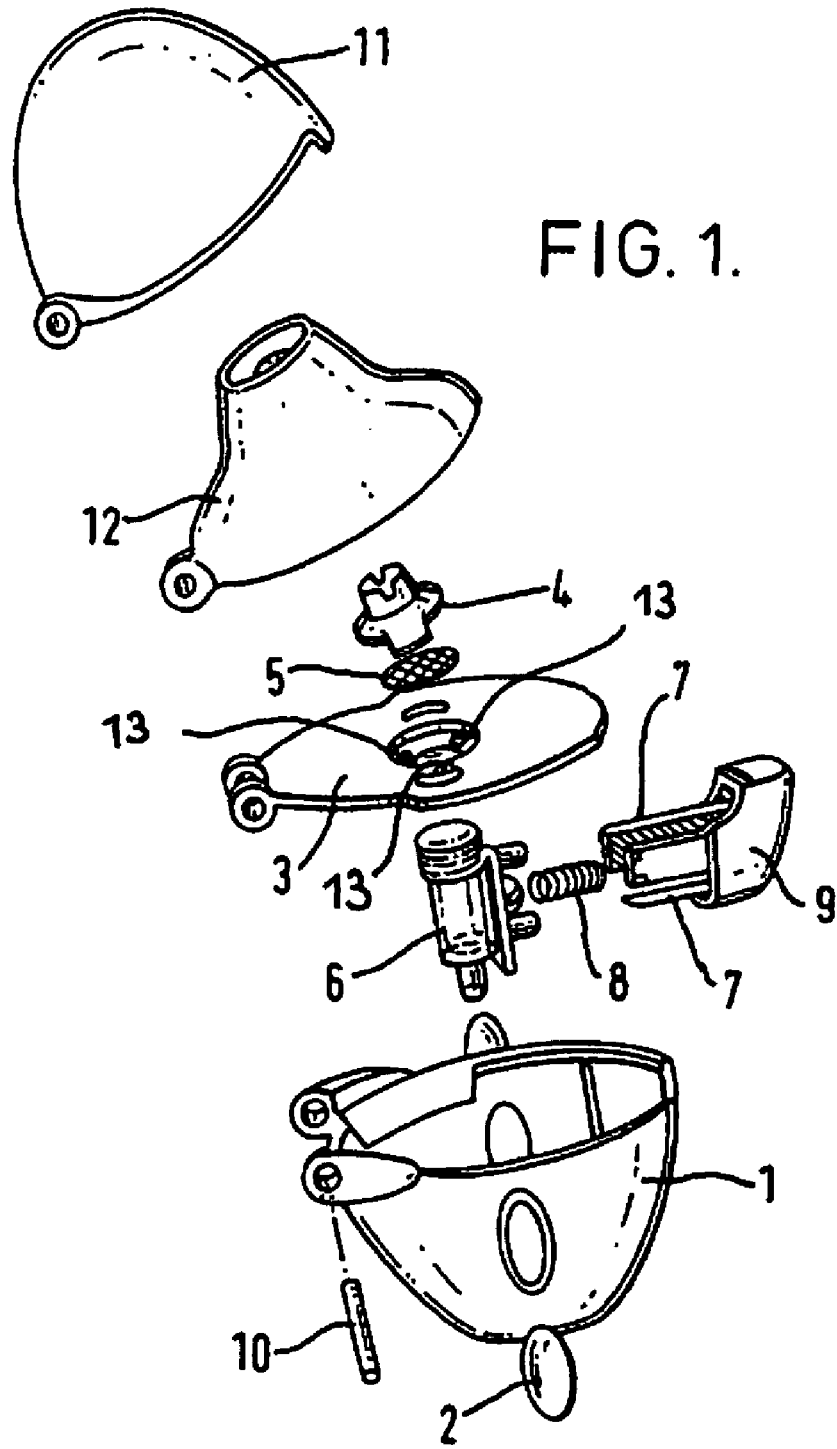

MEDICAMENTS FOR THE PREVENTION OR TREATMENT OF HEART FAILURE COMPRISING ADMINISTRATION OF AN ANTICHOLINERGIC

This application claims priority benefit under 35 USC 119(e) to U.S. Provisional Application 60/648,012, filed Jan. 28, 2005, which is incorporated by reference.

The present invention relates to a method for the prevention or treatment of heart failure comprising administration of a therapeutically effective amount of an anticholinergic 1, medicaments for the prevention or treatment of heart failure comprising one or more, preferably one anticholinergic 1, and methods for the preparation of these medicaments.

DESCRIPTION OF THE INVENTION

The present invention relates to a method for the prevention or the treatment of heart failure comprising administration of a therapeutically effective amount of an anticholinergic 1, optionally together with a pharmaceutically acceptable excipient.

In a preferred embodiment the invention relates to a method for the prevention or the treatment of heart failure comprising administration of a therapeutically effective amount of an anticholinergic 1 selected from among tiotropium salts, oxitropium salts, flutropium salts, ipratropium salts, glycopyrronium salts and trospium salts, optionally together with a pharmaceutically acceptable excipient.

In the above-mentioned salts the cations tiotropium, oxitropium, flutropium, ipratropium, glycopyrronium and trospium are the pharmacologically active components. Within the scope of the present patent application, an explicit reference to the above cations is indicated by the use of the number 1'. Any reference to the aforementioned salts 1 naturally also includes a reference to the ingredients 1' (tiotropium, oxitropium, flutropium, ipratropium, glycopyrronium or trospium). By the salts 1 which may be used within the scope of the present invention are meant the compounds which contain, in addition to tiotropium, oxitropium, flutropium, ipratropium, glycopyrronium or trospium as counter-ion (anion), chloride, bromide, iodide, sulphate, phosphate, methanesulphonate, nitrate, maleate, acetate, citrate, fumarate, tartrate, oxalate, succinate, benzoate or p-toluenesulphonate, wherein chloride, bromide, iodide, sulphate, methanesulphonate or para-toluenesulphonate are preferred. Within the scope of the present invention, the methanesulphonate, chloride, bromide and iodide are preferred of all the salts 1. If trospium salts are used the chloride is of particular importance. From the other salts mentioned hereinbefore the methanesulphonate and bromide are of particular importance. Of particular importance according to the invention are salts 1 selected from among tiotropium salts, oxitropium salts and ipratropium salts. Of outstanding importance according to the invention are salts 1 selected from among tiotropium bromide, oxitropium bromide and ipratropium bromide. Tiotropium bromide is particularly preferred. The aforementioned salts may be optionally present in form of their solvates or hydrates, preferably in form of their hydrates. If tiotropium bromide is used it is preferably present in form of its crystalline tiotropium bromide monohydrate as disclosed in WO 02/30928. In case tiotropium bromid is used in anhydrous form, it is preferably present in form of the crystalline tiotropium bromide anhydrate disclosed in WO 03/000265.

Optionally the anticholinergic agents mentioned hereinbefore possess chiral carbon centers. In this case the pharmaceutical compositions according to the invention may contain the anticholinergic agents in form of their enantiomers, mixtures of enantiomers or racemats. Preferably chiral anticholinergics are present in form of one of their pure enantiomers.

In another preferred embodiment the invention relates to a method for the prevention or the treatment of heart failure comprising administration of a therapeutically effective amount of an anticholinergic 1 selected from the salts of LAS 34273, being characterized by the formula 1a

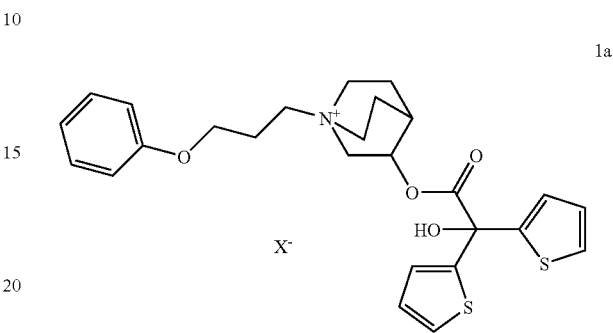

wherein
  $X^-$ denotes an anion with a single negative charge, preferably an anion selected from the group consisting of fluoride, chloride, bromide, iodide, sulphate, phosphate, methanesulphonate, nitrate, maleate, acetate, citrate, fumarate, tartrate, oxalate, succinate, benzoate and p-toluenesulphonate,
optionally in the form of the racemates, the enantiomers, and the hydrates thereof, and optionally together with a pharmaceutically acceptable excipient.

Within the method according to the invention, preferably the salts of formula 1a are used wherein
$X^-$ denotes an anion with a single negative charge selected from among the fluoride, chloride, bromide, 4-toluenesulphonate and methanesulphonate, preferably bromide,
optionally in the form of the racemates, the enantiomers, and the hydrates thereof.

More preferably, the salts of formula 1a are used wherein
$X^-$ denotes an anion with a single negative charge selected from among the chloride, bromide and methanesulphonate, preferably bromide,
optionally in the form of the racemates, the enantiomers, and the hydrates thereof.

Particularly preferred according to the invention is the salt of formula 1a wherein $X^-$ denotes bromide.

Of particular interest in the method according to the invention are the enantiomers of formula 1a-en

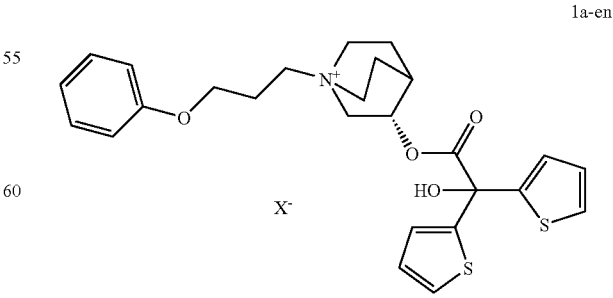

wherein $X^-$ may have the meanings as mentioned hereinbefore.

In a yet another preferred embodiment the invention relates to a method for the prevention or the treatment of heart failure comprising administration of a therapeutically effective amount of an anticholinergic 1 selected from the compounds of formula 1b

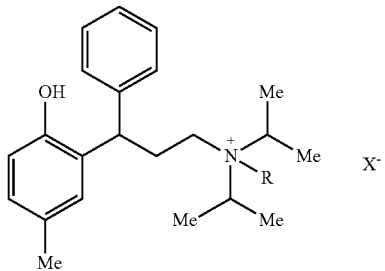

1b wherein R is either methyl or ethyl and wherein $X^-$ may have the meanings as mentioned hereinbefore. In the alternative the compound according to formula 1b may be present in form of its free base according to formula 1b-base

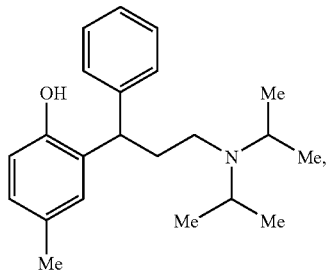

1b-base optionally together with a pharmaceutically acceptable excipient.

In the method according to the invention the anticholinergic agents of formula 1b (or 1b-base) may be applied in form of their enantiomers, mixtures of enantiomers or racemats. Preferably, the anticholinergic agent of formula 1b (or 1b-base) is applied in form of its R-enantiomer.

In a yet another preferred embodiment the invention relates to a method for the prevention or the treatment of heart failure comprising administration of a therapeutically effective amount of an anticholinergic 1 selected from the compounds of formula 1c

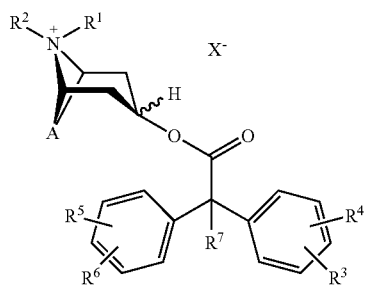

1c wherein
A denotes a double-bonded group selected from among

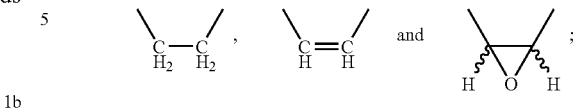

$X^-$ may have the meanings as mentioned hereinbefore, preferably chloride, bromide or methansulphonate, $R^1$ and $R^2$ which may be identical or different denote a group selected from among methyl, ethyl, n-propyl and iso-propyl, which may optionally be substituted by hydroxy or fluorine, preferably unsubstituted methyl;

$R^3$, $R^4$, $R^5$ and $R^6$, which may be identical or different, denote hydrogen, methyl, ethyl, methyloxy, ethyloxy, hydroxy, fluorine, chlorine, bromine, CN, $CF_3$ or $NO_2$;

$R^7$ denotes hydrogen, methyl, ethyl, methyloxy, ethyloxy, $-CH_2-F$, $-CH_2-CH_2-F$, $-O-CH_2-F$, $-O-CH_2-CH_2-F$, $-CH_2-OH$, $-CH_2-CH_2-OH$, $CF_3$, $-CH_2OMe$, $-CH_2-CH_2-OMe$, $-CH_2-OEt$, $-CH_2-CH_2-OEt$, $-O-COMe$, $-O-COEt$, $-O-COCF_3$, $-O-COCF_3$, fluorine, chlorine or bromine, optionally together with a pharmaceutically acceptable excipient.

The compounds of formula 1c are known in the art (WO 02/32899).

In a preferred embodiment of the invention the method comprises administration of compounds of formula 1c, wherein $X^-$ denotes bromide;

$R^1$ and $R^2$ which may be identical or different denote a group selected from methyl and ethyl, preferably methyl;

$R^3$, $R^4$, $R^5$ and $R^6$, which may be identical or different, denote hydrogen, methyl, methyloxy, chlorine or fluorine;

$R^7$ denotes hydrogen, methyl or fluorine, optionally together with a pharmaceutically acceptable excipient.

Of particular importance within the method according to the invention are compounds of general formula 1c, wherein A denotes a double-bonded group selected from among

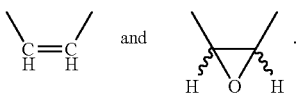

The compounds of formula 1c, may optionally be administered in the form of the individual optical isomers, mixtures of the individual enantiomers or racemates thereof.

Of particular importance within the method according to the invention are the following compounds of formula 1c:
tropenol 2,2-diphenylpropionic acid ester methobromide,
scopine 2,2-diphenylpropionic acid ester methobromide,
scopine 2-fluoro-2,2-diphenylacetic acid ester methobromide and
tropenol 2-fluoro-2,2-diphenylacetic acid ester methobromide.

In a yet another preferred embodiment the invention relates to a method for the prevention or the treatment of heart failure comprising administration of a therapeutically effective amount of an anticholinergic 1 selected from the compounds of formula 1d 1d wherein
A, X⁻, $R^1$ and $R^2$ may have the meanings as mentioned hereinbefore and wherein
$R^7$, $R^8$, $R^9$, $R^{10}$, $R^{11}$ and $R^{12}$, which may be identical or different, denote hydrogen, methyl, ethyl, methyloxy, ethyloxy, hydroxy, fluorine, chlorine, bromine, CN, $CF_3$ or $NO_2$, with the proviso that at least one of the groups $R^7$, $R^8$, $R^9$, $R^{10}$, $R^{11}$ and $R^{12}$ is not hydrogen,
optionally together with a pharmaceutically acceptable excipient.

The compounds of formula 1d are known in the art (WO 02/32898).

In a preferred embodiment of the invention the method comprises administration of compounds of formula 1d, wherein
A denotes a double-bonded group selected from among X⁻ denotes bromide;
$R^1$ and $R^2$ which may be identical or different denote methyl or ethyl, preferably methyl;
$R^7$, $R^8$, $R^9$, $R^{10}$, $R^{11}$ and $R^{12}$, which may be identical or different, denote hydrogen, fluorine, chlorine or bromine, preferably fluorine with the proviso that at least one of the groups $R^7$, $R^8$, $R^9$, $R^{10}$, $R^{11}$ and $R^{12}$ not hydrogen,
optionally together with a pharmaceutically acceptable excipient.

Of particular importance within the method according to the invention are the following compounds of formula 1d:
tropenol 3,3',4,4'-tetrafluorobenzilic acid ester methobromide,
scopine 3,3',4,4'-tetrafluorobenzilic acid ester methobromide,
scopine 4,4'-difluorobenzilic acid ester methobromide,
tropenol 4,4'-difluorobenzilic acid ester methobromide,
scopine 3,3'-difluorobenzilic acid ester methobromide, and
tropenol 3,3'-difluorobenzilic acid ester methobromide.

The pharmaceutical compositions according to the invention may contain the compounds of formula 1d optionally in the form of the individual optical isomers, mixtures of the individual enantiomers or racemates thereof.

In a yet another preferred embodiment the invention relates to a method for the prevention or the treatment of heart failure comprising administration of a therapeutically effective amount of an anticholinergic 1 selected from the compounds of formula 1e 1e wherein A and X⁻ may have the meanings as mentioned hereinbefore, and wherein
$R^{15}$ denotes hydrogen, hydroxy, methyl, ethyl, —$CF_3$, $CHF_2$ or fluorine;
$R^{1'}$ and $R^{2'}$ which may be identical or different denote $C_1$-$C_5$-alkyl which may optionally be substituted by $C_3$-$C_6$-cycloalkyl, hydroxy or halogen, or
$R^{1'}$ and $R^{2'}$ together denote a —$C_3$-$C_5$-alkylene-bridge;
$R^{13}$, $R^{14}$, $R^{13'}$ and $R^{14'}$ which may be identical or different denote hydrogen, —$C_1$-$C_4$-alkyl, —$C_1$-$C_4$-alkyloxy, hydroxy, —$CF_3$, —$CHF_2$, CN, $NO_2$ or halogen,
optionally together with a pharmaceutically acceptable excipient.

The compounds of formula 1e are known in the art (WO 03/064419).

In a preferred embodiment of the invention the method comprises administration of compounds of formula 1e, wherein
A denotes a double-bonded group selected from among X⁻ denotes an anion selected from among chloride, bromide and methanesulphonate, preferably bromide;
$R^{15}$ denotes hydroxy, methyl or fluorine, preferably methyl or hydroxy;
$R^{1'}$ and $R^{2'}$ which may be identical or different represent methyl or ethyl, preferably methyl;
$R^{13}$, $R^{14}$, $R^{13'}$ and $R^{14'}$ which may be identical or different represent hydrogen, —$CF_3$, —$CHF_2$ or fluorine, preferably hydrogen or fluorine,
optionally together with a pharmaceutically acceptable excipient.

In another preferred embodiment of the invention the method comprises administration of compounds of formula 1e, wherein
A denotes a double-bonded group selected from among X⁻ denotes bromide;
$R^{15}$ denotes hydroxy or methyl, preferably methyl;
$R^{1'}$ and $R^{2'}$ which may be identical or different represent methyl or ethyl, preferably methyl;

$R^{13}$, $R^{14}$, $R^{13'}$ and $R^{14'}$ which may be identical or different represent hydrogen or fluorine,
optionally together with a pharmaceutically acceptable excipient.

Of particular importance within the method according to the invention are the following compounds of formula 1e:
tropenol 9-hydroxy-fluorene-9-carboxylate methobromide;
tropenol 9-fluoro-fluorene-9-carboxylate methobromide;
scopine 9-hydroxy-fluorene-9-carboxylate methobromide;
scopine 9-fluoro-fluorene-9-carboxylate methobromide;
tropenol 9-methyl-fluorene-9-carboxylate methobromide;
scopine 9-methyl-fluorene-9-carboxylate methobromide.

The pharmaceutical compositions according to the invention may contain the compounds of formula 1e optionally in the form of the individual optical isomers, mixtures of the individual enantiomers or racemates thereof.

In a yet another preferred embodiment the invention relates to a method for the prevention or the treatment of heart failure comprising administration of a therapeutically effective amount of an anticholinergic 1 selected from the compounds of formula 1f

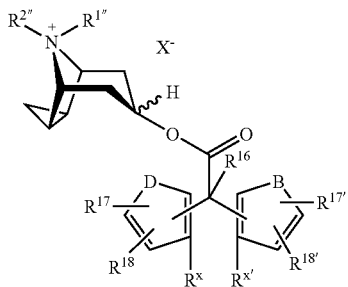

1f wherein $X^-$ may have the meanings as mentioned hereinbefore, and wherein
D and B which may be identical or different, preferably identical, denote —O—, —S—, —NH—, —CH$_2$—, —CH=CH—, or —N(C$_1$-C$_4$-alkyl)-;
$R^{16}$ denotes hydrogen, hydroxy, —C$_1$-C$_4$-alkyl, —C$_1$-C$_4$-alkyloxy, —C$_1$-C$_4$-alkylene-Halogen, —O—C$_1$-C$_4$-alkylene-halogen, —C$_1$-C$_4$-alkylene-OH, —CF$_3$, CHF$_2$, —C$_1$-C$_4$-alkylene-C$_1$-C$_4$-alkyloxy, —O—COC$_1$-C$_4$-alkyl, —O—COC$_1$-C$_4$-alkylene-halogen, —C$_1$-C$_4$-alkylene-C$_3$-C$_6$-cycloalkyl, —O—COCF$_3$ or halogen;
$R^{1'''}$ and $R^{2'''}$ which may be identical or different, denote —C$_1$-C$_5$-alkyl, which may optionally be substituted by —C$_3$-C$_6$-cycloalkyl, hydroxy or halogen, or
$R^{1'''}$ and $R^{2'''}$ together denote a —C$_3$-C$_5$-alkylene bridge;
$R^{17}$, $R^{18}$, $R^{17'}$ and $R^{18'}$ which may be identical or different, denote hydrogen, C$_1$-C$_4$-alkyl, C$_1$-C$_4$-alkyloxy, hydroxy, —CF$_3$, —CHF$_2$, CN, NO$_2$ or halogen;
$R^x$ and $R^{x'}$ which may be identical or different, denote hydrogen, C$_1$-C$_4$-alkyl, C$_1$-C$_4$-alkyloxy, hydroxy, —CF$_3$, —CHF$_2$, CN, NO$_2$ or halogen or
$R^x$ and $R^{x'}$ together denote a single bond or a bridging group selected from among the bridges —O—, —S—, —NH—, —CH$_2$—, —CH$_2$—CH$_2$—, —N(C$_1$-C$_4$-alkyl), —CH(C$_1$-C$_4$-alkyl)- and —C(C$_1$-C$_4$-alkyl)$_2$,
optionally together with a pharmaceutically acceptable excipient.

The compounds of formula 1f are known in the art (WO 03/064418).

In another preferred embodiment of the invention the method comprises administration of compounds of formula 1f wherein
$X^-$ denotes chloride, bromide, or methanesulphonate, preferably bromide;
D and B which may be identical or different, preferably identical, denote —O—, —S—, —NH— or —CH=CH—;
$R^{16}$ denotes hydrogen, hydroxy, —C$_1$-C$_4$-alkyl, —C$_1$-C$_4$-alkyloxy, —CF$_3$, —CHF$_2$, fluorine, chlorine or bromine;
$R^{1'''}$ and $R^{2'''}$ which may be identical or different, denote C$_1$-C$_4$-alkyl, which may optionally be substituted by hydroxy, fluorine, chlorine or bromine, or
$R^{1'''}$ and $R^{2'''}$ together denote a —C$_3$-C$_4$-alkylene-bridge;
$R^{17}$, $R^{18}$, $R^{17'}$ and $R^{18'}$, which may be identical or different, denote hydrogen, C1-C4-alkyl, C1-C4-alkyloxy, hydroxy, —CF3, —CHF2, CN, NO2, fluorine, chlorine or bromine;
$R^x$ and $R^{x'}$ which may be identical or different, denote hydrogen, C$_1$-C$_4$-alkyl, C$_1$-C$_4$-alkyloxy, hydroxy, —CF$_3$, —CHF$_2$, CN, NO$_2$, fluorine, chlorine or bromine or
$R^x$ and $R^{x'}$ together denote a single bond or a bridging group selected from among the bridges —O—, —S—, —NH— and —CH$_2$—,
optionally together with a pharmaceutically acceptable excipient.

In another preferred embodiment of the invention the method comprises administration of compounds of formula 1f, wherein
$X^-$ denotes chloride, bromide, or methanesulphonate, preferably bromide;
D and B which may be identical or different, preferably identical, denote —S— or —CH=CH—;
$R^{16''}$ denotes hydrogen, hydroxy or methyl;
$R^{1'''}$ and $R^{2'''}$ which may be identical or different, denote methyl or ethyl;
$R^{17}$, $R^{18}$, $R^{17'}$ and $R^{18'}$, which may be identical or different, denote hydrogen, —CF$_3$ or fluorine, preferably hydrogen;
$R^x$ and $R^{x'}$ which may be identical or different, denote hydrogen, —CF$_3$ or fluorine, preferably hydrogen or
$R^x$ and $R^{x'}$ together denote a single bond or the bridging group —O—,
optionally together with a pharmaceutically acceptable excipient.

In another preferred embodiment of the invention the method comprises administration of compounds of formula 1f, wherein
$X^-$ denotes bromide;
D and B denote —CH=CH—;
$R^{16}$ denotes hydrogen, hydroxy or methyl;
$R^{1'''}$ and $R^{2'''}$ denote methyl;
$R^{17}$, $R^{18}$, $R^{17'}$ and $R^{18'}$, which may be identical or different, denote hydrogen or fluorine, preferably hydrogen;
$R^x$ and $R^{x'}$ which may be identical or different, denote hydrogen or fluorine, preferably hydrogen or
$R^x$ and $R^{x'}$ together denote a single bond or the bridging group —O—,
optionally together with a pharmaceutically acceptable excipient.

Of particular importance within the method according to the invention are the following compounds of formula 1f:
cyclopropyltropine benzilate methobromide;
cyclopropyltropine 2,2-diphenylpropionate methobromide;
cyclopropyltropine 9-hydroxy-xanthene-9-carboxylate methobromide;

cyclopropyltropine 9-methyl-fluorene-9-carboxylate methobromide;
cyclopropyltropine 9-methyl-xanthene-9-carboxylate methobromide;
cyclopropyltropine 9-hydroxy-fluorene-9-carboxylate methobromide;
cyclopropyltropine methyl 4,4'-difluorobenzilate methobromide.

The pharmaceutical compositions according to the invention may contain the compounds of formula 1f optionally in the form of the individual optical isomers, mixtures of the individual enantiomers or racemates thereof.

In a yet another preferred embodiment the invention relates to a method for the prevention or the treatment of heart failure comprising administration of a therapeutically effective amount of an anticholinergic 1 selected from the compounds of formula 1g

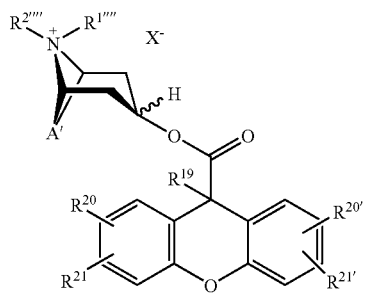

1g wherein $X^-$ may have the meanings as mentioned hereinbefore, and wherein
A' denotes a double-bonded group selected from among

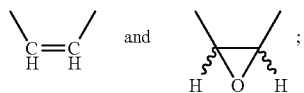

$R^{19}$ denotes hydroxy, methyl, hydroxymethyl, ethyl, —$CF_3$, $CHF_2$ or fluorine;
$R^{1'''}$ and $R^{2'''}$ which may be identical or different denote $C_1$-$C_5$-alkyl which may optionally be substituted by $C_3$-$C_6$-cycloalkyl, hydroxy or halogen, or
$R^{1'''}$ and $R^{2'''}$ together denote a —$C_3$-$C_5$-alkylene-bridge;
$R^{20}$, $R^{21}$, $R^{20'}$ and $R^{21'}$ which may be identical or different denote hydrogen, —$C_1$-$C_4$-alkyl, —$C_1$-$C_4$-alkyloxy, hydroxy, —$CF_3$, —$CHF_2$, CN, $NO_2$ or halogen,
optionally together with a pharmaceutically acceptable excipient.

The compounds of formula 1g are known in the art (WO 03/064417).

In another preferred embodiment of the invention the method comprises administration of compounds of formula 1g wherein
A' denotes a double-bonded group selected from among

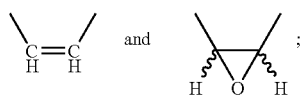

$X^-$ denotes chloride, bromide or methanesulphonate, preferably bromide;
$R^{19}$ denotes hydroxy or methyl;
$R^{1'''}$ and $R^{2'''}$ which may be identical or different represent methyl or ethyl, preferably methyl;
$R^{20}$, $R^{21}$, $R^{20'}$ and $R^{21'}$ which may be identical or different represent hydrogen, —$CF_3$, —$CHF_2$ or fluorine, preferably hydrogen or fluorine,
optionally together with a pharmaceutically acceptable excipient.

In another preferred embodiment of the invention the method comprises administration of compounds of formula 1g wherein
A' denotes a double-bonded group selected from among

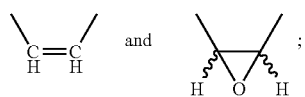

$X^-$ denotes bromide;
$R^{19}$ denotes hydroxy or methyl, preferably methyl;
$R^{1'''}$ and $R^{2'''}$ which may be identical or different represent methyl or ethyl, preferably methyl;
$R^3$, $R^4$, $R^{3'}$ and $R^{4'}$ which may be identical or different represent hydrogen or fluorine, optionally together with a pharmaceutically acceptable excipient.

Of particular importance within the method according to the invention are the following compounds of formula 1g:
tropenol 9-hydroxy-xanthene-9-carboxylate methobromide;
scopine 9-hydroxy-xanthene-9-carboxylate methobromide;
tropenol 9-methyl-xanthene-9-carboxylate methobromide;
scopine 9-methyl-xanthene-9-carboxylate methobromide;
tropenol 9-ethyl-xanthene-9-carboxylate methobromide;
tropenol 9-difluoromethyl-xanthene-9-carboxylate methobromide;
scopine 9-hydroxymethyl-xanthene-9-carboxylate methobromide.

The pharmaceutical compositions according to the invention may contain the compounds of formula 1g optionally in the form of the individual optical isomers, mixtures of the individual enantiomers or racemates thereof.

The alkyl groups used, unless otherwise stated, are branched and unbranched alkyl groups having 1 to 5 carbon atoms. Examples include: methyl, ethyl, propyl or butyl. The groups methyl, ethyl, propyl or butyl may optionally also be referred to by the abbreviations Me, Et, Prop or Bu. Unless otherwise stated, the definitions propyl and butyl also include all possible isomeric forms of the groups in question. Thus, for example, propyl includes n-propyl and iso-propyl, butyl includes iso-butyl, sec. butyl and tert.-butyl, etc.

The cycloalkyl groups used, unless otherwise stated, are alicyclic groups with 3 to 6 carbon atoms. These are the cyclopropyl, cyclobutyl, cyclopentyl and cyclohexyl groups. According to the invention cyclopropyl is of particular importance within the scope of the present invention.

The alkylene groups used, unless otherwise stated, are branched and unbranched double-bonded alkyl bridges with 1 to 5 carbon atoms. Examples include: methylene, ethylene, propylene or butylene.

The alkylene-halogen groups used, unless otherwise stated, are branched and unbranched double-bonded alkyl bridges with 1 to 4 carbon atoms which may be mono-, di- or trisubstituted, preferably disubstituted, by a halogen. Accordingly, unless otherwise stated, the term alkylene-OH groups denotes branched and unbranched double-bonded alkyl bridges with 1 to 4 carbon atoms which may be mono-, di- or trisubstituted, preferably monosubstituted, by a hydroxy.

The alkyloxy groups used, unless otherwise stated, are branched and unbranched alkyl groups with 1 to 5 carbon atoms which are linked via an oxygen atom. The following may be mentioned, for example: methyloxy, ethyloxy, propyloxy or butyloxy. The groups methyloxy, ethyloxy, propyloxy or butyloxy may optionally also be referred to by the abbreviations MeO, EtO, PropO or BuO. Unless otherwise stated, the definitions propyloxy and butyloxy also include all possible isomeric forms of the groups in question. Thus, for example, propyloxy includes n-propyloxy and iso-propyloxy, butyloxy includes iso-butyloxy, sec. butyloxy and tert.-butyloxy, etc. The word alkoxy may also possibly be used within the scope of the present invention instead of the word alkyloxy. The groups methyloxy, ethyloxy, propyloxy or butyloxy may optionally also be referred to as methoxy, ethoxy, propoxy or butoxy.

The alkylene-alkyloxy groups used, unless otherwise stated, are branched and unbranched double-bonded alkyl bridges with 1 to 5 carbon atoms which may be mono-, di- or trisubstituted, preferably monosubstituted, by an alkyloxy group.

The —O—CO-alkyl groups used, unless otherwise stated, are branched and unbranched alkyl groups with 1 to 4 carbon atoms which are bonded via an ester group. The alkyl groups are bonded directly to the carbonylcarbon of the ester group. The term —O—CO-alkyl-halogen group should be understood analogously. The group —O—CO—$CF_3$ denotes trifluoroacetate.

Within the scope of the present invention halogen denotes fluorine, chlorine, bromine or iodine. Unless otherwise stated, fluorine and bromine are the preferred halogens. The group CO denotes a carbonyl group.

The term "therapeutically effective amount" shall mean that amount of a drug or pharmaceutical agent that will elicit the biological or medical response of a tissue, system, animal or human that is being sought by a researcher or clinician.

For example, and without restricting the scope of the invention thereto, in the method according to the invention tiotropium may be administered for instance in such amounts that each individual dose contains 0.1-80 µg, preferably 0.5-60 µg, most preferably about 1-50µg. For example, and without restricting the scope of the invention thereto, 2.5 µg, 5 µg, 10 µg, 18 µg, 20 µg, 36 µg or 40 µg of tiotropium (calculation based on cation) may be administered per single dose.

For example, and without restricting the scope of the invention thereto, in the method according to the invention oxitropium may be administered for instance in such amounts that each individual dose contains 1-300 µg, preferably 5-250 µg, most preferably about 15-200 µg. For example, and without restricting the scope of the invention thereto, 15 µg, 25 µg, 35 µg, 45 µg, 55 µg, 65 µg, 75 µg, 85 µg, 95 µg, 105 µg, 115 µg, 125 µg, 135 µg, 145 µg, 155 µg, 165 µg, 175 µg, 185 µg or 195 µg of oxitropium (calculation based on cation) may be administered per single dose. Preferably the aforementioned doses are administered once, twice or three times per day, preferably twice or three times per day.

For example, and without restricting the scope of the invention thereto, in the method according to the invention flutropium may be administered for instance in such amounts that each individual dose contains 1-300 µg, preferably 5-250 µg, most preferably about 15-200 µg. For example, and without restricting the scope of the invention thereto, 15 µg, 25 µg, 35 µg, 45 µg, 55 µg, 65 µg, 75 µg, 85 µg, 95 µg, 105 µg, 115 µg, 125 µg, 135 µg, 145 µg, 155 µg, 165 µg, 175 µg, 185 µg or 195 µg of flutropium (calculation based on cation) may be administered per single dose. Preferably the aforementioned doses are administered once, twice or three times per day, preferably twice or three times per day.

For example, and without restricting the scope of the invention thereto, in the method according to the invention ipratropium may be administered for instance in such amounts that each individual dose contains 1-300 µg, preferably 5-250 µg, most preferably about 20-200 µg. For example, and without restricting the scope of the invention thereto, 25 µg, 35 µg, 45 µg, 55 µg, 65 µg, 75 µg, 85 µg, 95 µg, 105 µg, 115 µg, 125 µg, 135 µg, 145 µg, 155 µg, 165 µg, 175 µg, 185 µg or 195 µg of ipratropium (calculation based on cation) may be administered per single dose. Preferably the aforementioned doses are administered twice, three or four times per day, preferably twice or three times, more preferably three times per day.

For example, and without restricting the scope of the invention thereto, in the method according to the invention glycopyrronium may be administered for instance in such amounts that each individual dose contains 1-300 µg, preferably 5-250 µg, most preferably about 20-200 µg. For example, and without restricting the scope of the invention thereto, 25 µg, 35 µg, 45 µg, 55 µg, 65 µg, 75 µg, 85 µg, 95 µg, 105 µg, 115 µg, 125 µg, 135 µg, 145 µg, 155 µg, 165 µg, 175 µg, 185 µg or 195 µg of glycopyrronium (calculation based on cation) may be administered per single dose. Preferably the aforementioned doses are administered once, twice or three times per day, preferably twice or three times per day.

For example, and without restricting the scope of the invention thereto, in the method according to the invention compounds of formula 1c may be administered for instance in such amounts that each individual dose contains 1-300 µg, preferably 5-250 µg, most preferably about 20-200 µg. For example, and without restricting the scope of the invention thereto, 25 µg, 35 µg, 45 µg, 55 µg, 65 µg, 75 µg, 85 µg, 95 µg, 105 µg, 115 µg, 125 µg, 135 µg, 145 µg, 155 µg, 165 µg, 175 µg, 185 µg or 195 µg of 1c' may be administered per single dose. Preferably the aforementioned doses are administered once or twice per day, preferably once per day.

For example, and without restricting the scope of the invention thereto, in the method according to the invention compounds of formula 1d may be administered for instance in such amounts that each individual dose contains 1-300 µg, preferably 5-250 µg, most preferably about 20-200 µg. For example, and without restricting the scope of the invention thereto, 25 µg, 35 µg, 45 µg, 55 µg, 65 µg, 75 µg, 85 µg, 95 µg, 105 µg, 115 µg, 125 µg, 135 µg, 145 µg, 155 µg, 165 µg, 175 µg, 185 µg or 195 µg of 1d' may be administered per single dose. Preferably the aforementioned doses are administered once or twice per day, preferably once per day.

For example, and without restricting the scope of the invention thereto, in the method according to the invention compounds of formula 1e may be administered for instance in such amounts that each individual dose contains 1-250 µg, preferably 5-150 µg, most preferably about 10-100 µg. For example, and without restricting the scope of the invention thereto, 15 µg, 25 µg, 35 µg, 45 µg, 55 µg, 65 µg, 75 µg, 85 µg or 95 µg of 1e' may be administered per single dose. Preferably the aforementioned doses are administered once or twice per day, preferably once per day.

For example, and without restricting the scope of the invention thereto, in the method according to the invention compounds of formula 1f may be administered for instance in such amounts that each individual dose contains 1-300 µg, preferably 5-250 µg, most preferably about 20-200 µg. For example, and without restricting the scope of the invention thereto, 25 μg, 35 μg, 45 μg, 55 μg, 65 μg, 75 μg, 85 μg, 95 μg, 105 μg, 115 μg, 125 μg, 135 μg, 145 μg, 155 μg, 165 μg, 175 μg, 185 μg or 195 μg of 1f' may be administered per single dose. Preferably the aforementioned doses are administered once or twice per day, preferably once per day.

For example, and without restricting the scope of the invention thereto, in the method according to the invention compounds of formula 1g may be administered for instance in such amounts that each individual dose contains 1-250 μg, preferably 5-150 μg, most preferably about 10-100 μg. For example, and without restricting the scope of the invention thereto, 15 μg, 25 μg, 35 μg, 45 μg, 55 μg, 65 μg, 75 μg, 85 μg or 95 μg of 1g' may be administered per single dose. Preferably the aforementioned doses are administered once or twice per day, preferably once per day.

Within the scope of the present invention, any reference to the compounds 1' is to be regarded as a reference to the pharmacologically active cations contained in the salts 1. These are the cations tiotropium, oxitropium, flutropium, ipratropium, glycopyrronium, trospium or the cations of the following formulae

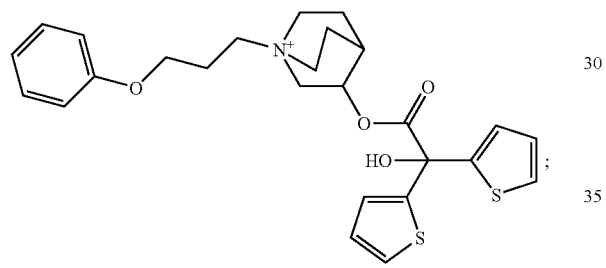

1a'

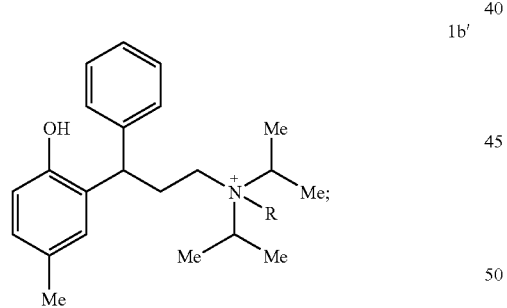

1b'

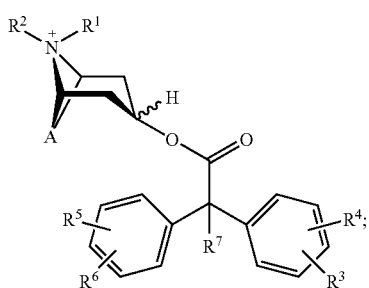

1c'

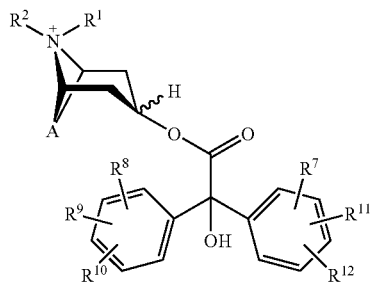

1d'

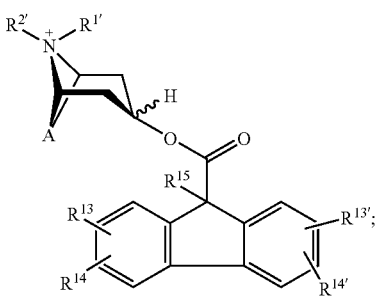

1e'

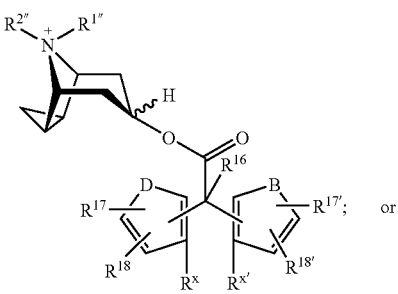

1f' or

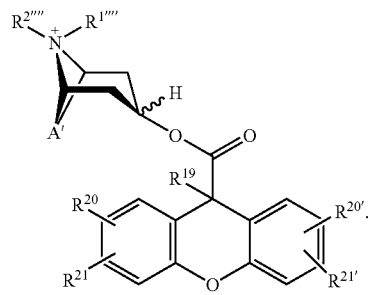

1g'

Heart failure is a common disorder of the heart, in which the contractility of the heart muscle (myocard) is impaired due to a variety of reasons, including artherosclerosis of the vessels of the heart (coronary artery disease), genetic conditions, and circulatory disturbances resulting from lung disease (pulmonary hypertension).

Decompensation of heart failure leads to pulmonary edema, a serious acute condition with significant mortality. The potential of tiotropium to ameliorate heart failure suggests a protecting effect of tiotropium on the development of pulmonary edema.

Accordingly, in another embodiment the invention is related to a method for the prevention 15 or the treatment of pulmonary edema, preferably of pulmonary associated with heart failure, comprising administration of a therapeutically effective amount of an anticholinergic 1, comprising the administration of a therapeutically effective amount of one or more, preferably one of the anticholinergic agents mentioned hereinbefore, optionally together with a pharmaceutically acceptable excipient.

Atrial fibrillation is a typical complication of heart failure. Congestion due to impaired contractility of the heart stretches muscle fibers of the vestibule of the heart, with the potential consequence of electrical instability of the cells which trigger rhythm abnormalities such as re-entry tachycardia leading to atrial flutter or atrial fibrillation. Hence, amelioration of heart failure by anticholinergics 1 decreases the risk of atrial fibrillation. Accordingly, in another embodiment the invention is related to a method for the prevention or the treatment of atrial fibrillation, comprising administration of a therapeutically effective amount of an anticholinergic 1, comprising the administration of a therapeutically effective amount of one or more, preferably one of the anticholinergic agents mentioned hereinbefore, optionally together with a pharmaceutically acceptable excipient.

In the method according to the invention the therapeutically effective amount of the anticholinergic may be optionally administered in combination with the therapeutically effective amount of another active ingredient 2. Preferably the second active ingredient is selected from among beta$_2$ agonists (also referred to as betamimetics), PDEIV-inhibitors, inhaled corticosteroids or LTB4-antagonists.

In the aforementioned pharmaceutical combinations the active substances may be combined in a single preparation or contained in two separate formulations.

Within the methods according to the invention preferably beta$_2$ agonists are co-administered with the anticholinergic agent. Preferred beta$_2$ agonists 2 in these combinations according to the invention are selected from the group consisting of albuterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmeterol, salmefamol, soterenot, sulphonterol, tiaramide, terbutaline, tolubuterol, CHF-1035, HOKU-81, KUL-1248, 3-(4-{6-[2-Hydroxy-2-(4-hydroxy-3-hydroxymethyl-phenyl)-ethylamino]-hexyloxy}-butyl)-benzenesulfoneamide, 5-[2-(5,6-Diethyl-indan-2-ylamino)-1-hydroxy-ethyl]-8-hydroxy-1H-quinolin-2-one, 4-hydroxy-7-[2-{[2-{[3-(2-phenylethoxy)propyl]sulphonyl}ethyl]-amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluormethylphenyl)-2-tert.-butylamino)ethanol and 1-(4-ethoxycarbonylamino-3-cyano-5-fluorophenyl)-2-(tert.-butylamino)ethanol, optionally in the form of the racemates, the enantiomers, the diastereomers and optionally the pharmacologically acceptable acid addition salts and the hydrates thereof.

According to the instant invention more preferred beta$_2$ agonists 2 are selected from the group consisting of bambuterol, bitolterol, carbuterol, clenbuterol, fenoterol, formoterol, hexoprenaline, ibuterol, pirbuterol, procaterol, reproterol, salmeterol, sulphonterol, terbutaline, tolubuterol, 3-(4-{6-[2-Hydroxy-2-(4-hydroxy-3-hydroxymethyl-phenyl)-ethylamino]-hexyloxy}-butyl)-benzenesulfoneamide, 5-[2-(5,6-Diethyl-indan-2-ylamino)-1-hydroxy-ethyl]-8-hydroxy-1H-quinolin-2-one, 4-hydroxy-7-[2-{[2-{[3-(2-phenylethoxy)propyl]sulphonyl}ethyl]-amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluormethylphenyl)-2-tert.-butylamino)ethanol and 1-(4-ethoxycarbonylamino-3-cyano-5-fluorophenyl)-2-(tert.-butylamino)ethanol, optionally in the form of the racemates, the enantiomers, the diastereomers and optionally the pharmacologically acceptable acid addition salts and the hydrates thereof.

More preferably, the betamimetics 2 used as within the compositions according to the invention are selected from among fenoterol, formoterol, salmeterol, 3-(4-{6-[2-Hydroxy-2-(4-hydroxy-3-hydroxymethyl-phenyl)-ethylamino]-hexyloxy}-butyl)-benzenesulfoneamide, 5-[2-(5,6-Diethyl-indan-2-ylamino)-1-hydroxy-ethyl]-8-hydroxy-1H-quinolin-2-one, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, optionally in the form of the racemates, the enantiomers, the diastereomers and optionally the pharmacologically acceptable acid addition salts thereof, and the hydrates thereof. Of the betamimetics mentioned above the compounds formoterol, salmeterol, 3-(4-{6-[2-Hydroxy-2-(4-hydroxy-3-hydroxymethyl-phenyl)-ethylamino]-hexyloxy}-butyl)-benzenesulfoneamide, and 5-[2-(5,6-Diethyl-indan-2-ylamino)-1-hydroxy-ethyl]-8-hydroxy-1H-quinolin-2-one are particularly preferred, optionally in the form of the racemates, the enantiomers, the diastereomers and optionally the pharmacologically acceptable acid addition salts thereof, and the hydrates thereof. Of the betamimetics mentioned above the compounds formoterol and salmeterol are particularly preferred, optionally in the form of the racemates, the enantiomers, the diastereomers and optionally the pharmacologically acceptable acid addition salts thereof, and the hydrates thereof.

Examples of pharmacologically acceptable acid addition salts of the betamimetics 2 according to the invention are the pharmaceutically acceptable salts which are selected from among the salts of hydrochloric acid, hydrobrornic acid, sulphuric acid, phosphoric acid, methanesulphonic acid, acetic acid, fumaric acid, succinic acid, lactic acid, citric acid, tartaric acid, 1-hydroxy-2-naphthalenecarboxylic acid, 4-phenylcinnamic acid, 5-(2,4-difluorophenyl)salicylic acid or maleic acid. If desired, mixtures of the abovementioned acids may also be used to prepare the salts 2.

According to the invention, the salts of the betamimetics 2 selected from among the hydrochloride, hydrobromide, sulphate, phosphate, fumarate, methanesulphonate, 4-phenylcinnamate, 5-(2,4-difluorophenyl)salicylate, maleate and xinafoate are preferred. Particularly preferred are the salts of 2 in the case of salmeterol selected from among the hydrochloride, sulphate, 4-phenylcinnamate, 5-(2,4-difluorophenyl)salicylate and xinafoate, of which the 4-phenylcinnamate, 5-(2,4-difluorophenyl)salicylate and especially xinafoate are particularly important. Particularly preferred are the salts of 2 in the case of formoterol selected from the hydrochloride, sulphate and fumarate, of which the hydrochloride and fumarate are particularly preferred. Of exceptional importance according to the invention is formoterol fumarate.

Salts of salmeterol, formoterol, 3-(4-{6-[2-Hydroxy-2-(4-hydroxy-3-hydroxymethyl-phenyl)-ethylamino]-hexyloxy}-butyl)-benzenesulfoneamide, and 5-[2-(5,6-Diethyl-indan-2-ylamino)-1-hydroxy-ethyl]-8-hydroxy-1H-quinolin-2-one, are preferably used as the betamimetics 2 according to the invention. Of particular importance according to the invention are salmeterol and formoterol salts. Any reference to the term betamimetics 2 also includes a reference to the relevant enantiomers or mixtures thereof.

In the pharmaceutical compositions according to the invention, the compounds 2 may be present in the form of their racemates, enantiomers or mixtures thereof. The separation of the enantiomers from the racemates may be carried out using methods known in the art (e.g. by chromatography on chiral phases, etc.) If the compounds 2 are used in the form of their enantiomers, it is particularly preferable to use the enantiomers in the R configuration at the C—OH group.

As an example, any reference to the most preferred compounds 2 according to the invention, the salts of salmeterol and formoterol, also includes the relevant enantiomeric salts of R-salmeterol, S-salmeterol, R,R-formoterol, S,S-formoterol, R,S-formoterol, S,R-formoterol and the mixtures thereof, while the enantiomeric salts of R-salmeterol and R,R-formoterol are of particular importance. The compounds 2 may also be present according to the invention in the form of the hydrates or solvates thereof.

Where the present invention refers to betamimetics which are not in the form of salts, this is indicated by a reference to compounds 2'. For example, the preferred betamimetics 2' according to the invention which are not in salt form include the free base of formoterol, salmeterol whereas the particularly preferred compounds 2 according to the invention are salmeterol xinafoate or formoterol fumarate.

Within the scope of the present invention the betamimetics 2 may possibly also be referred to as sympathomimetics or beta-2-agonists (β2-agonists). All these terms are to be regarded as interchangeable for the purposes of the present invention.

Within the methods according to the invention preferably steroids are co-administered with the anticholinergic agent. Preferred steroids 2 in these combinations according to the invention are selected from the group consisting of denote compounds selected from among methyl prednisolone, prednisone, butixocort propionate, RPR-106541, flunisolide, beclomethasone, triamcinolone, budesonide, fluticasone, mometasone, ciclesonide, rofleponide, ST-126, dexamethasone, 6α,9α-difluoro-17α-[(2-furanylcarbonyl)oxy]-11β-hydroxy-16α-methyl-3-oxo-androsta-1,4-diene-17β-carbothioic acid (S)-fluoromethyl ester, and 6α,9α-difluoro-11β-hydroxy-16α-methyl-3-oxo-17α-propionyloxy-androsta-1,4-diene-17β-carbothioic acid (S)-(2-oxo-tetrahydro-furan-3S-yl) ester.

Preferably, the steroid 2 is selected from among flunisolide, beclomethasone, triamcinolone, budesonide, fluticasone, mometasone, ciclesonide, rofleponide, ST-126, dexamethasone, 6α,9α-difluoro-17α-[(2-furanylcarbonyl)oxy]-11β-hydroxy-16α-methyl-3-oxo-androsta-1,4-diene-17β-carbothioic acid (S)-fluoromethyl ester, and 6α,9α-difluoro-11β-hydroxy-16α-methyl-3-oxo-17α-propionyloxy-androsta-1,4-diene-17β-carbothioic acid (S)-(2-oxo-tetrahydro-furan-3S-yl) ester. More preferably, the steroid 2 is selected from among budesonide, fluticasone, mometasone, ciclesonide, and 6α,9α-difluoro-17α-[(2-furanylcarbonyl)oxy]-11β-hydroxy-16α-methyl-3-oxo-androsta-1,4-diene-17β-carbothioic acid (S)-fluoromethyl ester, more preferably the steroid 2 is selected from among budesonide, fluticasone, mometasone, ciclesonide.

Any reference to steroids 2 within the scope of the present invention includes a reference to the salts or derivatives which may be formed from the steroids. Examples of possible salts or derivatives include: sodium salts, sulphobenzoates, phosphates, isonicotinates, acetates, propionates, dihydrogen phosphates, palmitates, pivalates or furoates. In some cases the steroids 2 may also occur in the form of their hydrates. Any reference to steroids 2 within the scope of the present invention also includes a reference to the steroids 2 in the form of their diastereomers, mixtures of diastereomers or in the form of the racemates.

The present invention also relates to the use of therapeutically effective quantities of the salts 1 for preparing a pharmaceutical composition for the prevention or treatment of heart failure. The present invention also relates to the use of therapeutically effective quantities of the salts 1 for preparing a pharmaceutical composition for the prevention or treatment of pulmonary edema, preferably of pulmonary associated with heart failure. The present invention also relates to the use of therapeutically effective quantities of the salts 1 for preparing a pharmaceutical composition for the prevention or treatment of atrial fibrillation.

The present invention preferably relates to the use of therapeutically effective quantities of the salts 1 for preparing a pharmaceutical composition for the prevention of heart failure. Furthermore, the present invention preferably relates to the use of therapeutically effective quantities of the salts 1 for preparing a pharmaceutical composition for the prevention of pulmonary edema, preferably of pulmonary associated with heart failure. Furthermore, the present invention preferably relates to the use of therapeutically effective quantities of the salts 1 for preparing a pharmaceutical composition for the prevention of atrial fibrillation.

In another preferred embodiment the present invention relates to the use of therapeutically effective quantities of the salts 1 for preparing a pharmaceutical composition for the treatment of heart failure. In another preferred embodiment the present invention preferably relates to the use of therapeutically effective quantities of the salts 1 for preparing a pharmaceutical composition for the treatment of pulmonary edema, preferably of pulmonary associated with heart failure. In another preferred embodiment the present invention preferably relates to the use of therapeutically effective quantities of the salts 1 for preparing a pharmaceutical composition for the treatment of atrial fibrillation.

Within the method according to the invention the anticholinergic and optionally another active ingredient are preferably administered by inhalation. Inhalable preparations according to the invention include inhalable powders, propellant-containing metered dose aerosols or propellant-free inhalable solutions. Inhalable powders according to the invention containing the active substances may consist of the active substances on their own or of a mixture of the active substances with physiologically acceptable excipients. Within the scope of the present invention, the term carrier may optionally be used instead of the term excipient. Within the scope of the present invention, the term propellant-free inhalable solutions also includes concentrates or sterile inhalable solutions ready for use.

These formulations which may be used within the scope of the present invention are described in more detail in the next part of the specification.

A) Inhalable Powders

The inhalable powders according to the invention may contain 1 (optionally combined with 2) either alone own or in admixture with suitable physiologically acceptable excipients. If the active substance 1 (optionally combined with 2) are present in admixture with physiologically acceptable excipients, the following physiologically acceptable excipients may be used to prepare these inhalable powders according to the invention: monosaccharides (e.g. glucose or arabinose), disaccharides (e.g. lactose, saccharose, maltose, trehalose), oligo- and polysaccharides (e.g. dextran), polyalcohols (e.g. sorbitol, mannitol, xylitol), cyclodextrines (e.g. α-cyclodextrine, β-cyclodextrine, χ-cyclodextrine, methyl-β-cyclodextrine, hydroxypropyl-β-cyclodextrine), salts (e.g. sodium chloride, calcium carbonate) or mixtures of these excipients with one another. Preferably, mono- or disaccharides are used, while the use of lactose, trehalose or glucose is preferred, particularly, but not exclusively, in the form of their hydrates.

Within the scope of the inhalable powders according to the invention the excipients have a maximum average particle size of up to 250 μm, preferably between 10 and 150 μm, most preferably between 15 and 80 μm. It may sometimes seem appropriate to add finer excipient fractions with an average particle size of 1 to 9 μm to the excipient mentioned above. These finer excipients are also selected from the group of possible excipients listed hereinbefore. Finally, in order to prepare the inhalable powders according to the invention, micronised active substance, preferably with an average particle size of 0.5 to 10 μm, more preferably from 1 to 6 μm, is added to the excipient mixture. Processes for producing the inhalable powders according to the invention by grinding and micronising and by finally mixing the ingredients together are known from the prior art.

The inhalable powders according to the invention may be administered using inhalers known from the prior art. Inhalable powders according to the invention which contain one or more physiologically acceptable excipients in addition to 1 may be administered, for example, by means of inhalers which deliver a single dose from a supply using a measuring chamber as described in U.S. Pat. No. 4,570,630, or by other means as described in DE 36 25 685. The inhalable powders according to the invention which contain 1 optionally in conjunction with a physiologically acceptable excipient may be administered, for example, using the inhaler known by the name Turbuhaler®, or using inhalers as disclosed for example in EP 237507. Preferably, the inhalable powders according to the invention which contain physiologically acceptable excipient in addition to 1 are packed into capsules (to produce so-called inhalettes) which are used in inhalers as described, for example, in WO 94/28958.

A particularly preferred inhaler for using the aformentioned pharmaceutical products within the method according to the invention is shown in FIG. 1.

This inhaler for inhaling powdered pharmaceutical compositions from capsules is characterised by a housing 1 containing two windows 2, a deck 3 in which there are air inlet ports and which is provided with a screen 5 secured via a screen housing 4, an inhalation chamber 6 connected to the deck 3 on which there is a push button 9 provided with two sharpened pins 7 and movable counter to a spring 8, and a mouthpiece 12 which is connected to the housing 1, the deck 3 and a cover 11 via a spindle 10 to enable it to be flipped open or shut, as well as airholes 13 for adjusting the flow resistance.

If the inhalable powders according to the invention are packed into capsules (inhalers) for the preferred use described above, the quantities packed into each capsule should be 1 to 30 mg per capsule.

B) Propellant Gas-Driven Inhalation Aerosols:

Inhalation aerosols containing propellant gas according to the invention may contain substance 1 dissolved in the propellant gas or in dispersed form. The propellant gases which may be used to prepare the inhalation aerosols according to the invention are known from the prior art. Suitable propellant gases are selected from among hydrocarbons such as n-propane, n-butane or isobutane and halohydrocarbons such as fluorinated derivatives of methane, ethane, propane, butane, cyclopropane or cyclobutane. The propellant gases mentioned above may be used on their own or in mixtures thereof. Particularly preferred propellant gases are halogenated alkane derivatives selected from TG11, TG12, TG134a (1,1,1,2-tetrafluoroethane) and TG227 (1,1,1,2,3,3,3-heptafluoropropane) and mixtures thereof, of which the propellant gases TG134a, TG227 and mixtures thereof are preferred.

The propellant-driven inhalation aerosols according to the invention may also contain other ingredients such as co-solvents, stabilisers, surfactants, antioxidants, lubricants and pH adjusters. All these ingredients are known in the art.

The inhalation aerosols containing propellant gas according to the invention may contain up to 5 wt.-% of active substance 1. Aerosols according to the invention contain, for example, 0.002 to 5 wt.-%, 0.01 to 3 wt.-%, 0.015 to 2 wt.-%, 0.1 to 2 wt.-%, 0.5 to 2 wt.-% or 0.5 to 1 wt.-% of active substance 1.

If the active substances 1 are present in dispersed form, the particles of active substance preferably have an average particle size of up to 10 μm, preferably from 0.1 to 6 μm, more preferably from 1 to 5 μm.

The propellant-driven inhalation aerosols according to the invention mentioned above may be administered using inhalers known in the art (MDIs=metered dose inhalers). Accordingly, in another aspect, the present invention relates to pharmaceutical compositions in the form of propellant-driven aerosols as hereinbefore described combined with one or more inhalers suitable for administering these aerosols. In addition, the present invention relates to inhalers which are characterised in that they contain the propellant gas-containing aerosols described above according to the invention. The present invention also relates to cartridges fitted with a suitable valve which can be used in a suitable inhaler and which contain one of the above-mentioned propellant gas-containing inhalation aerosols according to the invention. Suitable cartridges and methods of filling these cartridges with the inhalable aerosols containing propellant gas according to the invention are known from the prior art.

C) Propellant-Free Inhalable Solutions or Suspensions:

Propellant-free inhalable solutions and suspensions according to the invention contain, for example, aqueous or alcoholic, preferably ethanolic solvents, optionally ethanolic solvents mixed with aqueous solvents. If aqueous/ethanolic solvent mixtures are used the relative proportion of ethanol compared with water is not limited but preferably the maximum is up to 70 percent by volume, more particularly up to 60 percent by volume of ethanol. The remainder of the volume is made up of water. The solutions or suspensions containing 1 are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

According to the invention, the addition of editic acid (EDTA) or one of the known salts thereof, sodium editate, as stabiliser or complexing agent is unnecessary in the present formulation. Other embodiments may contain this compound or these compounds. In a preferred embodiment the content based on sodium editate is less than 100 mg/100 ml, preferably less than 50 mg/100 ml, more preferably less than 20 mg/100 ml. Generally, inhalable solutions in which the content of sodium editate is from 0 to 10 mg/100 ml are preferred.

Co-solvents and/or other excipients may be added to the propellant-free inhalable solutions according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents.

The preferred excipients include antioxidants such as ascorbic acid, for example, provided that it has not already been used to adjust the pH, vitamin A, vitamin E, tocopherols and similar vitamins and provitamins occurring in the human body.

Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art. The preservatives mentioned above are preferably present in concentrations of up to 50 mg/100 ml, more preferably between 5 and 20 mg/100 ml.

Preferred formulations contain, in addition to the solvent water and the active substances 1, only benzalkonium chloride and sodium editate. In another preferred embodiment, no sodium editate is present.

The propellant-free inhalable solutions according to the invention are administered in particular using inhalers of the kind which are capable of nebulising a small amount of a liquid formulation in the therapeutic dose within a few seconds to produce an aerosol suitable for therapeutic inhalation. Within the scope of the present invention, preferred inhalers are those in which a quantity of less than 100 μL, preferably less than 50 μL, more preferably between 20 and 30 μL of active substance solution can be nebulised in preferably one spray action to form an aerosol with an average particle size of less than 20 μm, preferably less than 10 μm, in such a way that the inhalable part of the aerosol corresponds to the therapeutically effective quantity.

An apparatus of this kind for propellant-free delivery of a metered quantity of a liquid pharmaceutical composition for inhalation is described for example in International Patent Application WO 91/14468 and also in WO 97/12687 (cf. in particular FIGS. 6a and 6b). The nebulisers (devices) described therein are known by the name Respimat®. This nebuliser (Respimat®) can advantageously be used to produce the inhalable aerosols according to the invention containing the active substances 1. Because of its cylindrical shape and handy size of less than 9 to 15 cm long and 2 to 4 cm wide, this device can be carried at all times by the patient. The nebuliser sprays a defined volume of pharmaceutical formulation using high pressures through small nozzles so as to produce inhalable aerosols.

The preferred atomiser essentially consists of an upper housing part, a pump housing, a nozzle, a locking mechanism, a spring housing, a spring and a storage container, characterised by
  a pump housing which is secured in the upper housing part and which comprises at one end a nozzle body with the nozzle or nozzle arrangement,
  a hollow plunger with valve body,
  a power takeoff flange in which the hollow plunger is secured and which is located in the upper housing part,
  a locking mechanism situated in the upper housing part,
  a spring housing with the spring contained therein, which is rotatably mounted on the upper housing part by means of a rotary bearing,
  a lower housing part which is fitted onto the spring housing in the axial direction.

The hollow plunger with valve body corresponds to a device disclosed in WO 97/12687. It projects partially into the cylinder of the pump housing and is axially movable within the cylinder. Reference is made in particular to FIGS. 1 to 4, especially FIG. 3, and the relevant parts of the description. The hollow plunger with valve body exerts a pressure of 5 to 60 Mpa (about 50 to 600 bar), preferably 10 to 60 Mpa (about 100 to 600 bar) on the fluid, the measured amount of active substance solution, at its high pressure end at the moment when the spring is actuated. Volumes of 10 to 50 microlitres are preferred, while volumes of 10 to 20 microlitres are particularly preferred and a volume of 15 microlitres per spray is most particularly preferred.

The valve body is preferably mounted at the end of the hollow plunger facing the valve body.

The nozzle in the nozzle body is preferably microstructured, i.e. produced by microtechnology. Microstructured nozzle bodies are disclosed for example in WO 94/07607;

reference is hereby made to the contents of this specification, particularly FIG. 1 therein and the associated description.

The nozzle body consists for example of two sheets of glass and/or silicon firmly joined together, at least one of which has one or more microstructured channels which connect the nozzle inlet end to the nozzle outlet end. At the nozzle outlet end there is at least one round or non-round opening 2 to 10 microns deep and 5 to 15 microns wide, the depth preferably being 4.5 to 6.5 microns while the length is preferably 7 to 9 microns. In the case of a plurality of nozzle openings, preferably two, the directions of spraying of the nozzles in the nozzle body may extend parallel to one another or may be inclined relative to one another in the direction of the nozzle opening. In a nozzle body with at least two nozzle openings at the outlet end the directions of spraying may be at an angle of 20 to 160° to one another, preferably 60 to 150°, most preferably 80 to 100°. The nozzle openings are preferably arranged at a spacing of 10 to 200 microns, more preferably at a spacing of 10 to 100 microns, most preferably 30 to 70 microns. Spacings of 50 microns are most preferred. The directions of spraying will therefore meet in the vicinity of the nozzle openings.

The liquid pharmaceutical preparation strikes the nozzle body with an entry pressure of up to 600 bar, preferably 200 to 300 bar, and is atomised into an inhalable aerosol through the nozzle openings. The preferred particle or droplet sizes of the aerosol are up to 20 microns, preferably 3 to 10 microns.

The locking mechanism contains a spring, preferably a cylindrical helical compression spring, as a store for the mechanical energy. The spring acts on the power takeoff flange as an actuating member the movement of which is determined by the position of a locking member. The travel of the power takeoff flange is precisely limited by an upper and lower stop. The spring is preferably biased, via a power step-up gear, e.g. a helical thrust gear, by an external torque which is produced when the upper housing part is rotated counter to the spring housing in the lower housing part. In this case, the upper housing part and the power takeoff flange have a single or multiple V-shaped gear.

The locking member with engaging locking surfaces is arranged in a ring around the power takeoff flange. It consists, for example, of a ring of plastic or metal which is inherently radially elastically deformable. The ring is arranged in a plane at right angles to the atomiser axis. After the biasing of the spring, the locking surfaces of the locking member move into the path of the power takeoff flange and prevent the spring from relaxing. The locking member is actuated by means of a button. The actuating button is connected or coupled to the locking member. In order to actuate the locking mechanism, the actuating button is moved parallel to the annular plane, preferably into the atomiser; this causes the deformable ring to deform in the annular plane. Details of the construction of the locking mechanism are given in WO 97/20590.

The lower housing part is pushed axially over the spring housing and covers the mounting, the drive of the spindle and the storage container for the fluid.

When the atomiser is actuated the upper housing part is rotated relative to the lower housing part, the lower housing part taking the spring housing with it. The spring is thereby compressed and biased by means of the helical thrust gear and the locking mechanism engages automatically. The angle of rotation is preferably a whole-number fraction of 360 degrees, e.g. 180 degrees. At the same time as the spring is biased, the power takeoff part in the upper housing part is moved along by a given distance, the hollow plunger is withdrawn inside the cylinder in the pump housing, as a result of which some of the fluid is sucked out of the storage container and into the high pressure chamber in front of the nozzle.

If desired, a number of exchangeable storage containers which contain the fluid to be atomised may be pushed into the atomiser one after another and used in succession. The storage container contains the aqueous aerosol preparation according to the invention. The atomising process is initiated by pressing gently on the actuating button. As a result, the locking mechanism opens up the path for the power takeoff member. The biased spring pushes the plunger into the cylinder of the pump housing. The fluid leaves the nozzle of the atomiser in atomised form.

Further details of construction are disclosed in PCT Applications WO 97/12683 and WO 97/20590, to which reference is hereby made.

The components of the atomiser (nebuliser) are made of a material which is suitable for its purpose. The housing of the atomiser and, if its operation permits, other parts as well, are preferably made of plastics, e.g. by injection moulding. For medicinal purposes, physiologically safe materials are used.

FIGS. 6a/b of WO 97/12687, show the nebuliser (Respimat®) which can advantageously be used for inhaling the aqueous aerosol preparations according to the invention.

FIG. 6a of WO 97/12687 shows a longitudinal section through the atomiser with the spring biased while FIG. 6b of WO 97/12687 shows a longitudinal section through the atomiser with the spring relaxed.

The upper housing part (51) contains the pump housing (52) on the end of which is mounted the holder (53) for the atomiser nozzle. In the holder is the nozzle body (54) and a filter (55). The hollow plunger (57) fixed in the power takeoff flange (56) of the locking mechanism projects partially into the cylinder of the pump housing. At its end the hollow plunger carries the valve body (58). The hollow plunger is sealed off by means of the seal (59). Inside the upper housing part is the stop (60) on which the power takeoff flange abuts when the spring is relaxed. On the power takeoff flange is the stop (61) on which the power takeoff flange abuts when the spring is biased. After the biasing of the spring the locking member (62) moves between the stop (61) and a support (63) in the upper housing part. The actuating button (64) is connected to the locking member. The upper housing part ends in the mouthpiece (65) and is sealed off by means of the protective cover (66) which can be placed thereon.

The spring housing (67) with compression spring (68) is rotatably mounted on the upper housing part by means of the snap-in lugs (69) and rotary bearing. The lower housing part (70) is pushed over the spring housing. Inside the spring housing is the exchangeable storage container (71) for the fluid (72) which is to be atomised. The storage container is sealed off by the stopper (73) through which the hollow plunger projects into the storage container and is immersed at its end in the fluid (supply of active substance solution). The spindle (74) for the mechanical counter is mounted in the covering of the spring housing. At the end of the spindle facing the upper housing part is the drive pinion (75). The slider (76) sits on the spindle.

The nebuliser described above is suitable for nebulising the aerosol preparations according to the invention to produce an aerosol suitable for inhalation.

If the formulation according to the invention is nebulised using the method described above (Respimat®) the quantity delivered should correspond to a defined quantity with a tolerance of not more than 25%, preferably 20% of this amount in at least 97%, preferably at least 98% of all operations of the inhaler (spray actuations). Preferably, between 5 and 30 mg of formulation, most preferably between 5 and 20 mg of formulation are delivered as a defined mass on each actuation.

However, the formulation according to the invention may also be nebulised by means of inhalers other than those described above, e.g. jet stream inhalers or other stationary nebulisers.

The Examples which follow serve to illustrate the present invention in more detail without restricting the scope of the invention to the following embodiments by way of example.

EXAMPLES OF FORMULATIONS

The following examples of formulations, which may be obtained analogously to methods known in the art, serve to illustrate the present invention more fully without restricting it to the contents of these examples.

Inhalable Powders:

| Ingredients | μg per capsule |
|---|---|
| 1) | |
| tiotropium bromide | 10.8 |
| lactose | 4989.2 |
| Total | 5000 |
| 2) | |
| tiotropium bromide | 21.7 |
| lactose | 4978.3 |
| Total | 5000 |
| 3) | |
| tiotropium bromide × H$_2$O | 22.5 |
| lactose | 4977.5 |
| Total | 5000 |
| 4) | |
| Iscopine 2,2-diphenylpropionic acid ester methobromide | 200 |
| Lactose | 23000 |
| Total | 25000 |
| 5) | |
| scopine 2,2-diphenylpropionic acid ester methobromide | 100 |
| Lactose | 12400 |
| Total | 12500 |
| 6) | |
| scopine 2,2-diphenylpropionic acid ester methobromide | 50 |
| Lactose | 4950 |
| Total | 5000 |
| 7) | |
| tropenol 2,2-diphenylpropionic acid ester methobromide | 200 |
| Lactose | 24800 |
| Total | 25000 |
| 8) | |
| scopine 3,3',4,4'-tetrafluorobenzilic acid ester methobromide | 100 |
| Lactose | 12400 |
| Total | 12500 |
| 9) | |
| scopine 4,4'-tetrafluorobenzilic acid ester methobromide | 100 |
| Lactose | 12400 |
| Total | 12500 |
| 10) | |
| tropenol 4,4'-tetrafluorobenzilic acid ester methobromide | 100 |
| Lactose | 12400 |
| Total | 12500 |
| 11) | |
| 1a-en (bromide) | 150 |
| Lactose | 12350 |
| Total | 12500 |
| 12) | |
| 1a-en (bromide) | 200 |
| Lactose | 24800 |
| Total | 25000 |
| 13) | |
| scopine 9-methyl-fluorene-9-carboxylate methobromide | 80 |
| Lactose | 12408 |
| Total | 12500 |
| 14) | |
| scopine 9-methyl-fluorene-9-carboxylate methobromide | 30 |
| Lactose | 12420 |
| Total | 12500 |
| 15) | |
| cyclopropyltropine 9-hydroxy-xanthene-9-carboxylate methobromide | 80 |
| Lactose | 12370 |
| Total | 12500 |
| 16) | |
| scopine 9-methyl-fluorene-9-carboxylate methobromide | 100 |
| Lactose | 24875 |
| Total | 25000 |
| 17) | |
| scopine 9-methyl-fluorene-9-carboxylate methobromide | 24 |
| Lactose | 4964 |
| Total | 5000 |
| 18) | |
| tropenol 9-methyl-fluorene-9-carboxylate methobromide | 24 |
| Lactose | 4964 |
| Total | 5000 |
| 19) | |
| tropenol 9-methyl-fluorene-9-carboxylate methobromide | 80 |
| Lactose | 12408 |
| Total | 12500 |
| 20) | |
| tropenol 9-methyl-fluorene-9-carboxylate methobromide | 30 |
| Lactose | 12420 |
| Total | 12500 |

-continued

| Ingredients | µg per capsule |
|---|---|
| 21) | |
| tropenol 9-methyl-fluorene-9-carboxylate methobromide | 100 |
| Lactose | 24875 |
| Total | 25000 |
| 22) | |
| tiotropium bromide | 10.8 |
| formoterol fumarate-dihydrate | 27.9 |
| lactose | 4961.3 |
| Total | 5000 |
| 23) | |
| tiotropium bromide | 21.7 |
| R,R-formoterol fumarate-dihydrate | 9.0 |
| lactose | 4969.3 |
| Total | 5000 |
| Total | 5000 |
| 24) | |
| tiotropium bromide × H$_2$O | 22.5 |
| salmeterol xinafoate | 35.0 |
| lactose | 4942.5 |
| Total | 5000 |
| 25) | |
| scopine 2,2-diphenylpropionic acid ester methobromide | 200 |
| R,R-formoterol fumarate-dihydrate | 12 |
| Lactose | 24788 |
| Total | 25000 |
| 26) | |
| scopine 2,2-diphenylpropionic acid ester methobromide | 100 |
| salmeterol xinafoate | 50 |
| Lactose | 12350 |
| Total | 12500 |
| 27) | |
| scopine 2,2-diphenylpropionic acid ester methobromide | 50 |
| formoterol fumarate dihydrate | 50 |
| Lactose | 4900 |
| Total | 5000 |
| 28) | |
| tropenol 2,2-diphenylpropionic acid ester methobromide | 200 |
| R,R-formoterol fumarate dihydrate | 24 |
| Lactose | 24776 |
| Total | 25000 |
| 29) | |
| scopine 3,3',4,4'-tetrafluorobenzilic acid ester methobromide | 100 |
| salmeterol xinafoate | 50 |
| Lactose | 12350 |
| Total | 12500 |
| 30) | |
| tropenol 3,3',4,4'-tetrafluorobenzilic acid ester methobromide | 100 |

-continued

| Ingredients | µg per capsule |
|---|---|
| salmeterol xinafoate | 50 |
| Lactose | 12350 |
| Total | 12500 |

B) Propellant-Containing Inhalable Aerosols:

| Ingredients | % by weight |
|---|---|
| 31) | |
| scopine 9-methyl-fluorene-9-carboxylate methobromide | 0.010 |
| Soya lecithin | 0.2 |
| TG 134a:TG 227 = 2:3 | ad 100 |
| 32) | |
| scopine 9-methyl-fluorene-9-carboxylate methobromide | 0.030 |
| absolute ethanol | 0.5 |
| Isopropyl myristate | 0.1 |
| TG 227 | ad 100 |
| 33) | |
| scopine 9-methyl-fluorene-9-carboxylate methobromide | 0.010 |
| Soya lecithin | 0.2 |
| TG 134a:TG 227 = 2:3 | ad 100 |
| 34) | |
| tiotropium bromide | 0.015 |
| soya lecithin | 0.2 |
| TG 134a:TG 227 = 2:3 | ad 100 |
| 35) | |
| tiotropium bromide | 0.029 |
| absolute ethanol | 0.5 |
| isopropyl myristate | 0.1 |
| TG 227 | ad 100 |
| 36) | |
| tiotropium bromide | 0.042 |
| absolute ethanol | 30 |
| purified water | 1.5 |
| anhydrous citric acid | 0.002 |
| TG 134a | ad 100 |
| 37) | |
| scopine 2,2-diphenylpropionic acid ester methobromide | 0.020 |
| Soya lecithin | 0.2 |
| TG 11:TG12 = 2:3 | ad 100 |
| 38) | |
| scopine 2,2-diphenylpropionic acid ester methobromide | 0.039 |
| absolute ethanol | 0.5 |
| Isopropyl myristate | 0.1 |
| TG 227 | ad 100 |
| 39) | |
| tropenol 2,2-diphenylpropionic acid ester methobromide | 0.020 |
| Soya lecithin | 0.2 |
| TG 11:TG12 = 2:3 | ad 100 |
| 40) | |
| tropenol 2,2-diphenylpropionic acid ester methobromide | 0.039 |
| absolute ethanol | 0.5 |
| Isopropyl myristate | 0.1 |
| TG 227 | ad 100 |

| Ingredients | % by weight |
|---|---|
| 41) | |
| tropenol 9-methyl-fluorene-9-carboxylate methobromide | 0.050 |
| Soya lecithin | 0.2 |
| TG 134a:TG 227 = 2:3 | ad 100 |
| 42) | |
| tropenol 9-methyl-fluorene-9-carboxylate methobromide | 0.080 |
| absolute ethanol | 0.5 |
| Isopropyl myristate | 0.1 |
| TG 227 | ad 100 |
| 43) | |
| tropenol 9-methyl-fluorene-9-carboxylate methobromide | 0.050 |
| Soya lecithin | 0.2 |
| TG 134a:TG 227 = 2:3 | ad 100 |

The invention claimed is:

1. A method for the treatment of pulmonary edema comprising administration of a therapeutically effective amount of an anticholinergic which is a tiotropium salt, optionally together with a pharmaceutically acceptable excipient.

2. A method for the treatment of atrial fibrillation comprising administration of a therapeutically effective amount of an anticholinergic which is a tiotropium salt, optionally together with a pharmaceutically acceptable excipient.

* * * * *